(12) United States Patent
Kurauchi et al.

(10) Patent No.: US 7,091,221 B2
(45) Date of Patent: Aug. 15, 2006

(54) PARTIAL ESTER OF CELLULOSE WITH NITROGENOUS CARBOXYLIC ACID AND PROCESS FOR PRODUCING THE SAME

(75) Inventors: Masahiko Kurauchi, Kanagawa (JP); Kiyonori Furuta, Kanagawa (JP); Hiroyuki Sato, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 340 days.

(21) Appl. No.: 10/168,384

(22) PCT Filed: Dec. 19, 2000

(86) PCT No.: PCT/JP00/08995

§ 371 (c)(1),
(2), (4) Date: Jun. 21, 2002

(87) PCT Pub. No.: WO01/46264

PCT Pub. Date: Jun. 28, 2001

(65) Prior Publication Data

US 2003/0027733 A1    Feb. 6, 2003

(30) Foreign Application Priority Data

Dec. 21, 1999  (JP) ............................. 11-362193
Aug. 21, 2000  (JP) ............................. 2000-249390

(51) Int. Cl.
*A61K 31/351* (2006.01)
*A61K 31/4433* (2006.01)
*A61K 31/4025* (2006.01)
*C07K 405/12* (2006.01)
*C07K 309/06* (2006.01)

(52) U.S. Cl. ............ 514/336; 514/397; 514/460; 546/282.1; 546/347; 548/311.1; 549/419

(58) Field of Classification Search ........... 549/419; 546/347, 282.1; 548/311.1; 514/336, 460, 514/397

See application file for complete search history.

(56) References Cited

U.S. PATENT DOCUMENTS

| 4,182,804 A | 1/1980 | Serboli et al |
| 5,017,229 A | 5/1991 | Burns et al |
| 5,097,023 A * | 3/1992 | Ducep et al. ............ 536/17.4 |

FOREIGN PATENT DOCUMENTS

WO    9220349    11/1992

OTHER PUBLICATIONS

Caplus Accession No: 1961:140073, abstract of Rogovin et al, "Vysokomoleckulyarnye Soedineniya 1" (1959), 157-61.*
Caplus Accession No: 1961:147109, abstract of Sun, T'ung et al, "Vysokomoleckulyarnye Soedineniya 2" (1960), 1768-71.*
Caplus Accession No: 1961:84365, abstract of Rogovin et al, "Zhurnal Prikladnoi Khimii 34" (1961), 350-6.*
Caplus Accession No: 1961:42983, abstract of Rogovin et al, "Mezhdunarod. Simpozium po Makromol. Khim." (1960), 302-9.*
Caplus Accession No: 1962:13683, abstract of Rogovin, Z.A. et al, "Vysokomoleckulyarnye Soedineniya 3" (1961), 1027-30.*
Caplus Accession No: 1962:67770, abstract of Sun, Tung et al."Vysokomoleckulyarnye Soedineniya 3" (1961), 1688-91.*
Caplus Accession No: 1962:39464, abstract of Rogovin, et al."Periodica Polytech." vol. 5 (2), 65-87.*

* cited by examiner

*Primary Examiner*—Joseph K. McKane
*Assistant Examiner*—Janet L. Coppins
(74) *Attorney, Agent, or Firm*—Oblon, Spivak, McClelland, Maier & Neustadt, P.C.

(57) ABSTRACT

According to the present invention, there are provided a novel partial ester of a nitrogenous carboxylic acid ester with cellulose, the partial ester being useful as an antibacterial agent, a flame retardant, etc., and a simple and convenient process for preparing the same. Fibers made of said partial ester have washing-resistant antibacterial property and flame retardancy.

There can be prepared the partial ester of a nitrogenous carboxylic acid ester with cellulose by contacting a nitrogenous carboxylic acid ester with cellulose and heat-treating the mixture.

10 Claims, No Drawings

PARTIAL ESTER OF CELLULOSE WITH NITROGENOUS CARBOXYLIC ACID AND PROCESS FOR PRODUCING THE SAME

TECHNICAL FIELD

The present invention relates to a novel partial ester of a nitrogenous carboxylic acid with cellulose or its salt, to an antibacterial agent and a flame retardant each containing the partial ester of cellulose with a nitrogenous carboxylic acid or its salt, to cellulose fibers having washing-resistant antibacterial property and flame retardancy such that antibacterial property- and flame retardancy-retaining powers are not lowered even by washing repeatedly and to a process for preparing the same. Also, the present invention relates to an antibacterial and flame retardancy-processing material for cellulose or cellulose fiber each containing a nitrogenous carboxylic acid ester.

BACKGROUND ART

Recently, various and novel antibacterial agents or antibacterial products have been put on the marketplaces under the background that the infection by methicillin resistant *Staphylococcus aures* (MRSA) and an infectious *Escherichia coli* O-157 became social problems. Among them, there is a fiber blend product of a natural high molecular compound having many amino groups such as chitosan and cellulose fibers or its viscose-mixed product. However, their effectiveness is limited and their antibacterial activity against *Escherichia coli* and *Pseudomonas auruginosa* is not necessarily sufficient. In addition, a means to impart antibacterial property into cellulose has been conducted by impregnating into it a metallic antibacterial agent such as silver phosphoric acid zirconium or silver zeolite or fixing the metallic antibacterial agent on it with a binder. However, these have problem that washing repeatedly lowers the antibacterial property. Also, an organic chemical, for example 10, 10'-oxybisphenoxyarsine and 2-(4-thiazolyl)-benzimidazole are known to be used. The former has a problem of toxicity because it contains arsenic while the latter has a problem of being corrosive toward metals. Therefore, there has been desired antibacterial cellulose or its fiber having washing-resistance and high safety.

As a means to impart flame retardancy into cellulose or its fiber, it is known to enhance the nitrogen content. However, there is no one which still retains flame retarclancy even by washing repeatedly and therefore one having washing-resistance has been desired.

As a means to impart washing-resistance and flame retardancy into cellulose or its fiber, although one utilizing hydroxy methylolation reaction is known, there is a problem of generating formalin.

On the other hand, as a process for preparing a partial ester of a nitrogenous carboxylic acid with cellulose, the preparation of glycine ester and aminoenathic acid ester is described in the abstract of "Z. A. Rogovin et al; Vysokomolekulyarne Soedincniya 1, 157–61 (1959)", the preparation of aminocaproic acid ester and amonoethic acid ester is described in the abstract of "Z. A. Rogovin et al; Periodica Polytech., 5, 65–87 (1961) and the preparation of glycine ester, alanine ester and aminocaproic acid ester is described in the abstract of "Z. A. Rogovin et al; Vysokomolekulyarne Soedincniya 3, 1027–30 (1961)". Also, the preparation of p-aminobenzoic acid ester and glycine ester is described in Japanese Patent Application Laid-Open No. Hei 1-249801. However, in all the preparation processes the reaction is conducted in the presence of organic solvents such as dimthylsulfoxide, dimethylformamide and pyridine, and therefore explosion-proof type of production equipment is needed in the production and recovery equipment of the solvents is also needed. In considering many restrictions imposed on the equipment and an influence of the solvents on environment and so on, they are not necessarily industrially desirable. Any of these known literatures makes no reference about the usefulness of the products or the partial esters of nitrogenous carboxylic acid with cellulose.

DISCLOSURE OF THE INVENTION

An object of the present invention is to solve the above problems and to provide cellulose or cellulose fibers having at least one of the effects of high antibacterial property and high flame retardancy, and further to provide an industrial process for preparing the same.

As a result of having ardently studied in the light of the above object, the present inventors have found that the above object may be solved by introducing a certain specific nitrogenous acyl group into cellulose and have completed the present invention.

That is, the present invention is a partial ester of a nitrogenous carboxylic acid with cellulose or its salt, said partial ester containing in the molecule chain at least one of glucose unit represented by the following general formula (I), in addition the present invention is fibers made of these constituent components and an antibacterial agent or a flame retardant containing them.

The terms "fibers whose constituent component a partial ester is a nitrogenous carboxylic acid with cellulose or its salt" in the present invention are ones wherein the surface layer of cellulose is partially esterified or chemically modified with a nitrogenous carboxylic acid as well as one which composes of a partial ester of a nitrogenous carboxylic acid with cellulose or its salt.

Among the partial esters of a nitrogenous carboxylic acid with cellulose which is represented by the following general formula (I), other ones are novel substances than ones wherein a nitrogenous carboxylic acid component is glycine, alanine, aminoenanthic acid, aminocaproic acid and p-aminobenzoic acid.

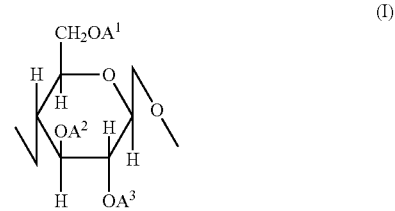

wherein $A^1$, $A^2$ and $A^3$ represent independently hydrogen atom or nitrogenous acyl group represented by the general formula (II) with a proviso that all of $A^1$, $A^2$ and $A^3$ are not hydrogen atoms.

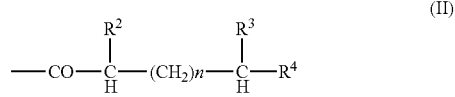

wherein R² represents hydrogen atom, an alkyl group having 1~6 carbon atoms, an amino group or a protonated amino group, R³ represents hydrogen atom, an alkyl group having 1~6 carbon atoms or an aryl group, R⁴ represents hydrogen atom, an alkyl group having 1~4 carbon atoms, hydroxyl group, mercapto group or a nitrogenous substituent represented by the general formulae (III)~(IX) and n represents an integer of 0~20. R² may bond with R³ to form a ring. In the case where R² is not an amino group or a protonated amino group, R⁴ is any one of the nitrogenous substituents represented by the general formulae (III)~(IX). In the case where R⁴ is not any one of the nitrogenous substituents represented by the general formulae (III)~(IX), R² is an amino group or a protonated amino group.

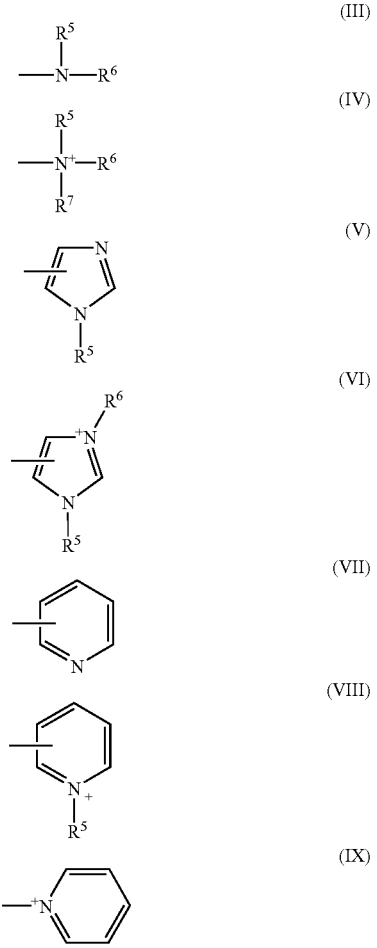

wherein $R^5$, $R^6$ and $R^7$ represent independently hydrogen atom, an alkyl group having 1~6 carbon atoms, an amino group, amidino group, nitroamidino group, protonated amino group or protonated amidino group, and, $R^5$ may bond with $R^2$, $R^3$ or $R^6$ to form a ring.

Also, the present inventors have found that the above object can be solved by contacting cellulose with a certain ester and heat-treating the mixture, and have completed the present invention.

That is, the present invention is a cellulose derivative or its salt, said cellulose derivative which is characterized by being obtained by a process which comprises contacting cellulose with a nitrogenous carboxylic acid ester represented by the general formula (X) and heat-treating the mixture and furthermore, the present invention is fibers composed of these constituent components, and an antibacterial agent or a flame retardant each containing them.

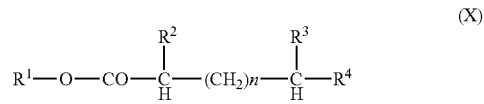

wherein $R^1$ represents an alkyl group having 1~7 carbon atoms, an aryl group or an aralkyl group, $R^2$, $R^3$, $R^4$ and n represent the same significance as those in the general formula (II)

Also, the present invention is an antibacterial processing agent and/or a flame retardant processing agent for cellulose or cellulose fiber which is characterized by containing a nitrogenous carboxylic acid ester represented by the general formula (X), and furthermore it is a process for preparing a partial ester of a nitrogenous carboxylic acid with cellulose or fibrous partial ester of a nitrogenous carboxylic acid with cellulose which is characterized by contacting cellulose or cellulose fibers with one of said antibacterial processing agent and said flame retardant processing agent and heat-treating the mixture.

Also, the present invention is a process for imparting an antibacterial property and/or a flame retardancy into cellulose fibers which is characterized by contacting cellulose fibers with a nitrogenous carboxylic acid ester represented by the general formula (X) and heat-treating the mixture.

In the partial esters of a nitrogenous carboxylic acid with cellulose which contains in the molecule chain at least one of glucose unit represented by the general formula (I) involving in the present invention, $R^2$ is hydrogen atom, an alkyl group having 1~6 carbon atoms, an amino group or a protonated amino group, preferably an amino group. Also, $R^3$ is hydrogen atom, an alkyl group having 1~6 carbon atoms or an aryl group, preferably hydrogen atom or phenyl group. $R^3$ is hydrogen atom, an alkyl group having 1~4 carbon atoms, hydroxyl group, mercapto group or a nitrogenous substituent represented by the general formulae (III)~(IX), preferably hydrogen atom, hydroxyl group or a nitrogenous substituent represented by the general formula (III) or (V), and n is an integer of 0~20, preferably 0~3.

The nitrogenous carboxylic acid moiety in the partial esters of a nitrogenous carboxylic acid with cellulose which involves in the present invention may be mixture of several kinds of ones. Also, the esterification degree in the partial ester of a nitrogenous carboxylic acid with cellulose is 0.00001 to 3 and in this range the functions of antibacterial property, flame retardancy, etc. may be exerted.

Specific examples of the partial esters of the nitrogenous carboxylic acid with cellulose which involves in the present invention include lysine cellulose partial ester, arginine cellulose partial ester, ornitine cellulose partial ester, histidine cellulose partial ester, phenylalanine cellulose partial ester and the like. The partial esters of a nitrogenous carboxylic acid with cellulose which involves in the present invention may be converted into its salt form by neutralizing with an acid. Examples of an acid to be used include organic acids such as acetic acid, lactic acid, malic acid, tartaric acid, succinic acid, citric acid, benzoic acid, pyrrolidone carboxylic acid, p-toluenesulfonic acid and ethanephosphonic acid; inorganic acids such as hydrochloric acid, sulfuric acid and phosphoric acid; inorganic acid esters or Lewis acid such as dodecyl sulfuric acid and phytic acid.

As cellulose which may be employed as a raw material in the present invention there may be used without difficulty any one of fibrous ones such as cotton, pulp and rayon, membrane-like one such as cellophane and powdered one such as microcrystalline cellulose. Also, there may be used fiber processed into sheet-like articles such as paper and cloth. Cellulose may be one pre-treated with an alkali, etc. by the usual manner depending on the necessity.

In the nitrogenous carboxylic acid ester represented by the general formula (X) which may be used in the present invention, although $R^1$ is an alkyl group having 1~7 carbon atoms, aryl group or aralkyl group, it is preferably an alkyl group having 1~4 carbon atoms, more preferably methyl group from the viewpoint of the easiness in the reactivity with cellulose. $R^2$ is hydrogen atom, an alkyl group having 1~6 carbon atoms, an amino group or a protonated amino group, preferably an amino group. Also, $R^3$ is hydrogen atom, an alkyl group having 1~6 carbon atoms or an aryl group, preferably hydrogen atom or phenyl group. $R^4$ is hydrogen atom, an alkyl group having 1~4 carbon atoms, hydroxyl group, mercapto group or a nitrogenous substituent represented by the general formulae (III)~(IX), preferably hydrogen atom, hydroxyl group or a nitrogenous substituent represented by the general formula (III) or (V). n is an integer of 0~20, preferably 0~3.

Specific examples of a nitrogenous carboxylic acid ester include lysine methyl ester, arginine methyl ester, ornithine methyl ester, histidine methyl ester, phenylalanine methyl ester and the like.

In either case where a nitrogenous carboxylic acid ester which may be employed in the present invention is used as an antibacterial processing agent and/or a flame retardant processing agent or where it is used for preparing a partial ester of a nitrogenous carboxylic acid with cellulose, it is dissolved in water or an alcohol or their mixed solvent or otherwise it may be in the state of being dispersed or being partially crystallized with turbidity or being gelatinous. In these cases, the nitrogenous carboxylic acid ester content may be in such a range that it is dissoluble or dispersible in the solvent. The nitrogenous carboxylic acid ester may be free one or a salt with mineral acid such as hydrochloride.

Also, a catalyst and/or a surfactant may be added depending on the necessity.

The form of an antibacterial agent and/or a flame retardant which is characterized by containing a partial ester of a nitrogenous carboxylic acid with cellulose is not limited particularly and it may be any one including liquid, stick, solid, mousse, film, aerosol and the like.

The partial ester of a nitrogenous carboxylic acid with cellulose in the present invention may be prepared by contacting cellulose with a nitrogenous carboxylic acid ester represented by the general formula (X) and heat-treating the mixture.

As the contacting method, cellulose is immersed in a solvent wherein a nitrogenous carboxylic acid ester has been dissolved or dispersed and thereafter the excessive solvent is removed suitably and followed by drying. In addition, spraying, brushing surface adhesion and so on may be applied. Especially, suitable removal of an excessive solvent after immersion of cellulose in the solvent and the subsequent drying procedure are the most preferred for achieving uniform contact between cellulose and a nitrogenous carboxylic acid ester.

As to the drying means, there is no problem in either case of air drying or drying under heating. In the case of air-drying, the drying condition is 1 to 24 hours, preferably 2 to 6 hours at room temperature. In the case of drying under heating, the drying condition is 5 to 120 minutes, preferably 10 to 60 minutes at 30~100° C., preferably 50~80° C.

By this drying, the esterification proceeds as dry reaction.

The condition for the heat treatment is not restricted particularly so long as the esterification proceeds. Usually, the temperature is 100 to 200° C., preferably 120 to 180° C. and the heating time is 1 to 100 minutes, preferably 5 to 60 minutes.

The heating apparatus is not restricted particularly, but a batch type hot air furnace, a continuous hot air heating furnace, an infrared ray heating furnace, contact heating apparatus by heating plate, heating rollers and the like may be employed.

As the reaction catalyst to be added depending on the necessity, there may be taken mineral acids such as phosphoric acid, sulfuric acid and the like or Lewis acids such as zinc chloride and the like. However, in considering influence of them on the environment, etc., especially phosphoric acid or its salt is preferred. Although the content of it in the treating agent solution is optional but usually it may be 1 to 100 mol % based on the nitrogenous carboxylic acid ester used.

As the surfactant to be added depending on the necessity, either an ionic or non-ionic surfactant may be employed. Although the content of it in the treating agent solution is optional but usually it may be 0.5 to 50 weight % based on the nitrogenous carboxylic acid ester used.

The fibers for use in the present invention may be any form of the literal fibrous articles, bundle articles and woven cloth articles.

THE BEST MODE FOR CARRYING OUT THE INVENTION

The present invention is further illustrated by the following Examples but it is not restricted thereto.

The nitrogenous carboxylic acid formed ester-bond with cellulose was confirmed by spraying ninhydrin to a sample and heating the sample to cause coloring. The confirmation of ester bond was conducted by measuring the respective spectra of untreated specimen and treated specimen with an infrared spectroscopic analyzer (Parkin Elmer Spectrum One) and observing the difference between both the spectra. As to whether or not free nitrogenous carboxylic acid ester employed as a raw material is present, 0.5 g of a sample was immersed in 10 ml of water for a hour at room temperature and thereafter the eluate was analyzed with a HPLC. When said nitrogenous carboxylic acid ester was not detected, the absence of it was confirmed. The bonded amount of a nitrogenous carboxylic acid was determined by a process wherein about 0.5 g of the sample dried a overnight at 50° C. under vacuum weighed accurately and was immersed in 50 ml of 5 N sodium hydroxide at room temperature for 18 to 24 hours under stirring to effect alkaline hydrolysis, and thereafter analysis was conducted with an amino acid analyzer (L-8500, a product of Hitachi Co., Ltd.). An organic acid was analyzed with a HPLC, and identified and quantatively determined by comparison with an authentic sample.

EXAMPLE 1

4.66 Grams (20 mmol) of L-lysine methyl ester dihydrochloride, 2.22 g (6.2 mmol) of disodium phosphate 12 hydrate and 0.2 g of polyoxyethylene lauryl ether ("Newcol 1100", nonionic surfactant produced by Nippon Nyukazai Co., Ltd.) were dissolved in 10.0 ml of water to prepare a treating agent solution. A cotton cloth (200 mm×200 mm, 7.5 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous citric acid solution and rinsed three times with water, and finally washed with household washing detergent solution, rinsed with water and air-dried. The identification of the formed L-lysine cellulose ester was conducted by the following method. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1720–1740 $cm^{-1}$. Furthermore, 0.5 g of the cloth was immersed in 10 ml of pure water for an hour at room temperature and then the immersed water was analyzed by HPLC whereby it was confirmed that free L-lysine methyl ester was not eluted. As a result of determination for the amount of the L-lysine bonded, it was 0.17 mmol per g of the cloth. The degree of esterfication was 0.028. Also, the amount of citric acid was 0.15 mmol.

EXAMPLE 2

5.22 Grams (20 mmol) of L-arginine methyl ester dihydrochloride, 2.22 g (6.2 mmol) of disodium phosphate 12 hydrate and 0.2 g of polyoxyethylene lauryl ether ("Newcol 1100", nonionic surfactant produced by Nippon Nyukazai Co., Ltd.1 were dissolved in 10.0 ml of water to prepare a treating agent solution. A cotton cloth (200 mm×200 mm, 7.5 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous citric acid solution and rinsed three times with water, and finally washed with household washing detergent solution, rinsed with water and air-dried. The identification of the amino acid cellulose ester was conducted by the following method. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1720–1740 $cm^{-1}$. Furthermore, 0.5 g of the cloth was immersed in 10 ml of water for an hour at room temperature and then this aqueous solution was analyzed by HPLC whereby it was confirmed that free L-arginine methyl ester was not remained at all. As a result of determination for the amount of the L-arginine bonded, it was 0.15 mmol per g of the cloth. The degree of esterfication was 0.024. Also, the amount of citric acid was 0.16 mmol.

EXAMPLE 3

4.84 Grams (20 mmol) of L-histidine methyl ester dihydrochloride, 2.22 g (6.2 mmol) of disodium phosphate 12 hydrate and 0.2 g of polyoxyethylene lauryl ether ("Newcol 1100", nonionic surfactant produced by Nippon Nyukazai Co., Ltd.) were dissolved in 10.0 ml of water to prepare a treating agent solution. A cotton cloth (200 mm×200 mm, 7.5 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous citric acid solution and rinsed three times with water, and finally washed with household washing detergent solution, rinsed with water and air-dried. The identification of the L-histidine cellulose ester was conducted by the following method. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis. As a result, there was confirmed a peak based on ester bond at 1720–1740 $cm^{-1}$. Furthermore, 0.5 g of the cloth was immersed in 10 ml of water for 5 hours at room temperature and then this aqueous solution was analyzed by HPLC whereupon free L-histidine methyl ester was confirmed not to remain. As a result of determination for the amount of the L-histidine bonded, it was 0.11 mmol based on 1 g of the cloth. The degree of esterfication was 0.018. Also, the amount of citric acid was 0.08 mmol.

EXAMPLE 4

2.33 Grams (10 mmol) of L-lysine methyl ester dihydrochloride, 1.11 g (3.1 mmol) of disodium phosphate 12 hydrate and 0.1 g of polyoxyethylene lauryl ether ("Newcol 1100", nonionic surfactant produced by Nippon Nyukazai Co., Ltd.) were dissolved in 5.0 ml of water to prepare a treating agent solution. A cotton cloth (150 mm×170 mm, 4.8 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous succinic acid solution and rinsed three times with water, and finally washed with household washing detergent solution, rinsed with water and air-dried. The identification of L-lysine cellulose ester was conducted by the following method. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1730–1750 cm$^{-1}$. As a result of determination for the amount of the L-lysine bonded, it was 0.19 mmol based on 1 g of the cloth. The degree of esterfication was 0.031. Also, the amount of succinic acid was 0.39 mmol.

EXAMPLE 5

2.61 Grams (10 mmol) of L-arginine methyl ester dihydrochloride, 1.11 g (3.1 mmol) of disodium phosphate 12 hydrate and 0.1 g of polyoxyethylene lauryl ether ("Newcol 1100", nonionic surfactant produced by Nippon Nyukazai Co., Ltd.) were dissolved in 5.0 ml of water to prepare a treating agent solution. A cotton cloth (150 mm×170 mm, 4.8 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently was washed with 10% aqueous succinic acid solution and rinsed three times with water, and finally washed with household washing detergent solution, rinsed with water and air-dried. The identification of L-arginine cellulose ester was conducted by the following method. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1730–1750 cm$^{-1}$. As a result of determination for the amount of the bonded L-arginine, it was 0.22 mmol based on 1 g of the cloth. The degree of esterfication was 0.036. Also, the amount of succinic acid was 0.34 mmol.

EXAMPLE 6

2.42 Grams (10 mmol) of L-histidine methyl ester dihydrochloride, 1.11 g (3.1 mmol) of disodium phosphate 12 hydrate and 0.1 g of polyoxyethylene lauryl ether ("Newcol 1100", nonionic surfactant produced by Nippon Nyukazai Co., Ltd.) were dissolved in 5.0 ml of water to prepare a treating agent solution. A cotton cloth (150 mm×170 mm, 4.8 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous succinic acid solution and rinsed three times with water, and finally washed with household washing detergent solution, rinsed with water and air-dried. The identification of L-histidine cellulose ester was conducted by the following method. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1730–1750 cm$^{-1}$. As a result of determination for the amount of the bonded L-histidine, it was 0.17 mmol based on 1 g of the cloth. The degree of esterfication was 0.028. Also, the amount of succinic acid was 0.18 mmol.

EXAMPLE 7

A similar manner as in Example 4 was conducted except that washing with PCA (L-2-pyrrolidone-5-carboxylic acid) was conducted in place of washing with succinic acid. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1730–1750 cm$^1$. As a result of determination for the amount of the bonded L-lysine, it was 0.17 mmol based on 1 g of the cloth. The degree of esterfication was 0.028. Also, the amount of PCA was 0.18 mmol.

EXAMPLE 8

A similar manner as in Example 5 was conducted except that washing with PCA (L-2-pyrrolidone-5-carboxylic acid) was conducted in place of washing with succinic acid. A part of the cloth was cut and a solution of ninhydrin in butanol was sprayed on it. Thereafter, it was placed for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1730–1750 cm$^{-1}$. As a result of determination for the amount of the bonded L-arginine, it was 0.18 mmol based on 1 g of the cloth. The degree of esterfication was 0.029. Also, the amount of PCA was 0.26 mmol.

EXAMPLE 9

A similar manner as in Example 6 was conducted except that washing with PCA (L-2-pyrrolidone-5-carboxylic acid) was conducted in place of washing with succinic acid. A part of the cloth was cut and a solution of ninhydrin in butanol was sprayed on it. Thereafter, it was placed for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1730–1750 cm$^{-1}$. As a result of determination for the amount of the bonded L-histidine, it was 0.16 mmol based on 1 g of the cloth. The degree of esterfication was 0.026. Also, the amount of PCA was 0.22 mmol.

EXAMPLE 10

A similar manner as in Example 4 was conducted except that washing with succinic acid was omitted. A part of the cloth was cut and a solution of ninhydrin in butanol was sprayed on it. Thereafter, it was placed for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1720–1740 cm$^{-1}$. As a result of determination for the amount of the bonded L-lysine, it was 0.18 mmol based on 1 g of the cloth. The degree of esterfication was 0.029.

EXAMPLE 11

A similar manner as in Example 5 was conducted except that washing with succinic acid was omitted. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1720–1740 cm$^{-1}$. As a result of determination for the amount of the bonded L-arginine, it was 0.18 mmol based on 1 g of the cloth. The degree of esterfication was 0.029.

EXAMPLE 12

A similar manner as in Example 6 was conducted except that washing with succinic acid was omitted. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1720–1740 cm$^{-1}$. As a result of determination for the amount of the bonded L-histidine, it was 0.17 mmol based on 1 g of the cloth. The degree of esterfication was 0.028.

EXAMPLE 13

A similar manner as in Example 4 was conducted except that the cotton cloth was used without being treated with an aqueous sodium hydroxide solution. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1720–1740 cm$^{-1}$. As a result of determination for the amount of the bonded L-arginine, it was 0.08 mmol based on 1 g of the cloth. The degree of esterfication was 0.013.

EXAMPLE 14

2.33 Grams (10 mmol) of L-lysine methyl ester dihydrochloride was dissolved in 5.0 ml of water to prepare a treating agent solution. A cotton cloth (150 mm×170 mm, 4.8 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently was washed with 10% aqueous citric acid solution and rinsed three times with water, and finally washed with household washing detergent solution, rinsed with water and air-dried. The identification of L-lysine cellulose ester was conducted by the following method. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1720–1740 cm$^{1}$. As a result of determination for the amount of the L-lysine bonded, it was 0.10 mmol based on 1 g of the cloth. The degree of esterfication was 0.016.

EXAMPLE 15

2.61 Grams (10 mmol) of L-arginine methyl ester dihydrochloride, 1.11 g (3.1 mmol) of disodium phosphate 12 hydrate and 0.1 g of polyoxyethylene lauryl ether ("Newcol 1100", nonionic surfactant produced by Nippon Nyukazai Co., Ltd.) were dissolved in 5.0 ml of water to prepare a treating agent solution. A cotton cloth (150 mm×170 mm, 4.8 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 40 minutes at 150° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently was washed with 10% aqueous citric acid solution and rinsed three times with water, and finally washed with household washing detergent solution, rinsed with water and air-dried. The identification of L-arginine cellulose ester was conducted by the following method. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1720–1740 cm$^{-1}$. As a result of determination for the amount of the bonded L-arginine, it was 0.08 mmol based on 1 g of the cloth. The degree of esterfication was 0.013.

EXAMPLE 16

2.61 Grams (10 mmol) of L-arginine methyl ester dihydrochloride, 1.11 g (3.1 mmol) of disodium phosphate 12 hydrate and 0.1 g of polyoxyethylene lauryl ether ("Newcol 1100", nonionic surfactant produced by Nippon Nyukazai Co., Ltd.) were dissolved in 5.0 ml of water to prepare a treating agent solution. A cotton cloth (150 mm×170 mm, 4.8 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 40 minutes at 150° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and then washed with 5% aqueous phosphoric acid solution and rinsed twice with water. Subsequently it was immersed in 5% aqueous phosphoric acid solution for 10 minutes, and thereafter was rinsed with water and air-dried. A part of the cloth was cut and a solution of ninhydrin in butanol was sprayed on it. Thereafter, it was heated for 10 minutes in an oven of 110° C. to cause coloring thereby the presence of the amino acid was confirmed. The amount of the bonded L-arginine was 0.08 mmol based on 1 g of the cloth. The degree of esterfication was 0.013.

EXAMPLE 17

20.88 Grams (90 mmol) of L-lysine methyl ester dihydrochloride was dissolved in 18 ml of methanol, and 45 ml of 2 N aqueous sodium hydroxide solution was added thereto to prepare a treating agent solution. An untreated cotton cloth (480 mm×510 mm, 45 g) was allowed to uniformly absorb the total amount of the above treating agent solution and then air-dried for 2 hours at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently was washed with 10% aqueous citric acid solution and rinsed three times with water, and finally washed with household washing detergent solution, rinsed with water and air-dried. A part of the cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1742 cm$^{-1}$. As a result of determination for the amount of the L-lysine bonded, it was 0.10 mmol based on 1 g of the cloth. The degree of esterfication was 0.0 16.

EXAMPLE 18

2.62 Grams (10 mmol) of L-lysine n-propyl ester dihydrochloride was dissolved in 2 ml of methanol, and 5 ml of 2 N aqueous sodium hydroxide solution was added thereto to prepare a treating agent solution. An untreated cotton cloth (160 mm×170 mm, 5.0 g) was allowed to uniformly absorb the total amount of the above treating agent solution and then air-dried for an hour and 15 minutes at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently was washed with 10% aqueous citric acid solution and rinsed three times with water, and finally washed with household washing detergent solution, rinsed with water and air-dried. A part of the cloth was cut and a solution of ninhydrin in butanol was sprayed on it. Thereafter, it was heated for 10 minutes in an oven of 110° C. to cause coloring thereby the presence of the amino acid was confirmed. As a result of determination for the amount of the bonded L-lysine, it was 0.08 mmol based on 1 g of the cloth. The degree of esterfication was 0.013.

EXAMPLE 19

1.56 Gram (6 mmol) of L-arginine methyl ester dihydrochloride, 3 ml of 2 N aqueous sodium hydroxide solution and 7 ml of methanol were mixed together to prepare a treating agent solution. To the treating agent solution was added 3.0 g of powdered cellulose (KC flock "W-400G", a product of Nippon Paper Industries Co., Ltd.) and then air-dried for 1.5 hour at room temperature. The dried matter was heat-treated for 40 minutes at 140° C. in a batch type hot air oven ("IPHH-2000", an inert oven manufactured by Tabaiesbeck Co., Ltd.). The heat-treated material was cooled to room temperature and thereafter 50 ml of water was added thereto to make a slurry, which was filtered under suction and washed. It was further washed twice with water, done with 5% aqueous sodium bicarbonate solution and rinsed twice with water and then washed with 10% aqueous citric acid solution, rinsed twice with water and dried under reduced pressure to yield 2.43 g of powdered L-arginine cellulose ester. On a part of powdered L-arginine cellulose ester was sprayed a solution of ninhydrin in butanol. Thereafter, it was heated for 10 minutes in an oven of 110° C. to cause coloring thereby the presence of the amino acid was confirmed. Also, it was subjected to an infrared spectroscopic analysis whereby there was confirmed a peak based on ester bond at 1720–1740 cm$^{-1}$. As a result of determination for the amount of the bonded L-arginine present in powdered L-arginine cellulose ester, it was 0.02 mmol based on 1 g of the cloth. The degree of esterfication was 0.003.

EXAMPLE 20

1.16 Gram (5 mmol) of L-lysine methyl ester dihydrochloride was dissolved in 4.5 ml of methanol, and 2.5 ml of 2 N aqueous sodium hydroxide solution was added thereto to prepare a treating agent solution. An untreated cotton cloth (160 mm×170 mm, 5.0 g) was allowed to uniformly absorb the total amount of the above treating agent solution and then air-dried for an hour at room temperature. The dried cloth was heat-treated for 20 minutes at 140° C. in a batch type hot air oven ("IPHH-2000", an inert oven manufactured by Tabaiesbeck Co., Ltd.) and then washed with water. It was further washed with 5% aqueous sodium bicarbonate solution and rinsed three times with water and subsequently was washed with 0.05 N aqueous hydrochloric acid solution and rinsed three times with water, and finally washed with a JAFET standard detergent solution for household washing machine, rinsed with water and air-dried. A part of this cloth was cut and a solution of ninhydrin in butanol was sprayed on it. Thereafter, it was heated for 10 minutes in an oven of 110° C. to cause coloring thereby the presence of the amino acid was confirmed. Also, a part of the cloth was cut and subjected to an infrared spectroscopic analysis whereby there was confirmed a peak based on ester bond at 1749 cm$^{-1}$. As a result of determination for the amount of the bonded L-lysine, it was 0.10 mmol based on 1 g of the cloth. The degree of esterfication was 0.016.

EXAMPLE 21

1.31 Gram (5 mmol) of L-arginine methyl ester dihydrochloride was dissolved in 4 ml of methanol, and 2.5 ml of 2 N aqueous sodium hydroxide solution was added thereto to prepare a treating agent solution. An untreated cotton cloth (160 mm×170 mm, 5.0 g) was allowed to uniformly absorb the total amount of the above treating agent solution and then air-dried for an hour at room temperature. The dried cloth was heat-treated for 20 minutes at 140° C. in a batch type hot air oven ("IPHH-2000", an inert oven manufactured by Tabaiesbeck Co., Ltd.) and then washed with water. It was further washed with 5% aqueous sodium bicarbonate solution and rinsed three times with water and subsequently washed with 10% aqueous citric acid solution and rinsed three times with water, and finally washed with a JAFET standard detergent solution for household washing machine, rinsed with water and air-dried. A part of this cloth was cut and a solution of ninhydrin in butanol was sprayed on it. Thereafter, it was heated for 10 minutes in an oven of 110° C. to cause coloring thereby the presence of the amino acid was confirmed. As a result of determination for the amount of the bonded L-arginine, it was 0.08 mmol based on 1 g of the cloth. The degree of esterfication was 0.013.

EXAMPLE 22

2.33 Grams (10 mmol) of L-lysine methyl ester dihydrochloride was dissolved in 15 ml of methanol, and 5 ml of 2 N aqueous sodium hydroxide solution was added thereto to prepare a treating agent solution. 5.0 Grams of cotton nonwoven fabric ("C×32", a product of Hanylon Co., Ltd.) was immersed in the treating agent solution and then air-dried for an hour. The dried nonwoven fabric was heat-treated for 20 minutes at 140° C. in a batch type hot air oven ("IPHH-2000", an inert oven manufactured by Tabaiesbeck Co., Ltd.) and then washed with water. It was further washed with 5% aqueous sodium bicarbonate solution and rinsed three times with water and subsequently washed with 10% aqueous citric acid solution and rinsed three times with water, and thereafter dehydrated and air-dried to prepare a sample. A part of this sample was dried at 50° C. overnight under vacuum and about 0.5 g of it weighed accurately and was stirred in 50 ml of 0.5 N aqueous sodium hydroxide solution for 18 hours at room temperature to effect alkaline hydrolysis. The fiber was filtered out and the determination of L-lysine was conducted using an amino acid analyzer ("L-8500", a product of Hitachi Co., Ltd.). From the result, the amount of the bonded L-lysine per g of the sample was calculated to be 0.11 mmol. The degree of esterfication was 0.018. Also, from the result of determination for citric acid present in the same test solution using HPLC, the amount of the bonded citric acid per g of the sample was calculated to be 0.19 mmol.

EXAMPLE 23

A similar experiment was conducted as in Example 22 except that 2.61 g (10 mmol) of L-arginine methyl ester dihydrochloride was used in place of L-lysine methyl ester dihydrochloride. The amount of the bonded L-arginine and that of the bonded citric acid per 1 g of the sample were calculated in the similar manner as in Example 22 and the results indicate 0.11 mmol (the degree of esterification: 0.018), 0.16 mmol, respectively.

EXAMPLE 24

2.70 Grams (10 mmol) of $N^\delta$-nitro-L-arginine methyl ester dihydrochloride, 1.11 g (3.1 mmol) of disodium phosphate 12 hydrate and 0.1 g of polyoxyethylene lauryl ether ("Newcol 1100", nonionic surfactant produced by Nippon Nyukazai Co., Ltd.) were dissolved in 4.5 ml of water to prepare a treating agent solution. A cotton cloth (150 mm×170 mm, 4.8 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 4.5 hours at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous citric acid solution and rinsed three times with water, and finally washed with household washing detergent solution, rinsed with water and air-dried. A part of the cloth was cut and a solution of ninhydrin in butanol was sprayed on it. Thereafter, it was heated for 10 minutes in an oven of 110° C. to cause coloring thereby the presence of the amino acid was confirmed.

EXAMPLE 25

2.16 Grams (10 mmol) of L-phenylalanine methyl ester hydrochloride, 1.11 g (3.1 mmol) of disodium phosphate 12 hydrate and 0.1 g of polyoxyethylene lauryl ether ("Newcol 1100", a nonionic surfactant produced by Nippon Nyukazai Co., Ltd.) were dissolved in 4.5 ml of water to prepare a treating agent solution. A cotton cloth (150 mm×170 mm, 4.8 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous citric acid solution and rinsed three times with water, and finally washed with household detergent solution for washing, rinsed with water and air-dried. A part of the cloth was cut and a solution of ninhydrin in butanol was sprayed on it. Thereafter, it was heated for 10 minutes in an oven of 110° C. to cause coloring thereby the presence of the amino acid was confirmed. As a result of determination for the amount of the bonded L-phenylalanine, it was 0.16 mmol per g of the cloth. The degree of esterification was 0.026.

EXAMPLE 26

2.51 Grams (20 mmol) of glycine methyl ester hydrochloride, 1.11 g (3.1 mmol) of disodium phosphate 12 hydrate and 0.1 g of polyoxyethylene lauryl ether ("Newcol 1100", nonionic surfactant produced by Nippon Nyukazai Co., Ltd.) were dissolved in 4.5 ml of water to prepare a treating agent solution. A cotton cloth (150 mm×170 mm, 4.8 g) was in advance treated to be immersed in 25% aqueous sodium hydroxide solution for an hour at room temperature, washed with water and dried. This treated cotton cloth was allowed to uniformly absorb the total amount of the above treating agent solution and then air-dried for 3 hours at room temperature. The dried cloth was heat-treated for 20 minutes at 150° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous citric acid solution and rinsed three times with water, and finally washed with household detergent solution for washing, rinsed with water and air-dried. A part of the cloth was cut and a solution of ninhydrin in butanol was sprayed on it. Thereafter, it was heated for 10 minutes in an oven of 110° C. to cause coloring thereby the presence of the amino acid was confirmed. As a result of determination for the amount of the bonded glycine, it was 0.06 mmol per g of the cloth. The degree of esterification was 0.010.

EXAMPLE 27

1.54 Gram (10 mmol) of β-alanine ethyl ester hydrochloride was dissolved in 5 ml of 2 N aqueous sodium hydroxide solution, and 2 ml of methanol was added thereto to prepare a treating agent solution. An untreated cotton cloth (160 mm×170 mm, 5.0 g) was was allowed to uniformly absorb the total amount of the above treating agent solution and then air-dried for 1.5 hour at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous citric acid solution and rinsed three times with water, and finally washed with household detergent solution for washing, rinsed with water and air-dried. A part of the cloth was cut and a solution of ninhydrin in butanol was sprayed on it. Thereafter, it was placed for 10 minutes in an oven of 110° C. to cause coloring thereby the presence of the amino acid was confirmed.

EXAMPLE 28

A similar procedure was conducted as in Example 27 except that 1.54 g (10 mmol) of γ-aminobutyric acid methyl ester hydrochloride was used in place of β-alanine ethyl ester hydrochloride.

EXAMPLE 29

A similar procedure was conducted as in Example 27 except that 1.82 g (10 mmol) of ε-aminocaproic acid methyl ester hydrochloride was used in place of β-alanine ethyl ester hydrochloride.

EXAMPLE 30

A similar procedure was conducted as in Example 27 except that 1. 94 g (10 mmol) of 3-aminocyclohexane carboxylic acid methyl ester hydrochloride was used in place of β-alanine ethyl ester hydrochloride.

EXAMPLE 31

1.57 Gram (10 mmol) of isonipecotinic acid ethyl ester hydrochloride was dissolved in 5 ml of methanol to prepare a treating agent solution. An untreated cotton cloth (160 mm×170 mm, 5.0 g) was allowed to uniformly absorb the total amount of the above treating agent solution and then air-dried for 30 minutes at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous citric acid solution and rinsed three times with water, and finally washed with household detergent solution for washing, rinsed with water and air-dried. A part of the cloth was cut and a solution of ninhydrin in butanol was sprayed on it. Thereafter, it was heated for 10 minutes in an oven of 110° C. to cause coloring thereby the presence of the amino acid was confirmed.

EXAMPLE 32

1.37 Gram (5 mmol) of 4-pyridiniobutyric acid ethyl ester bromide was dissolved in 4 ml of methanol, and 2.5 ml of 2 N aqueous sodium hydroxide solution was added thereto to prepare a treating agent solution. An untreated cotton cloth (160 mm×170 mm, 5.0 g) was allowed to uniformly absorb the total amount of the above treating agent solution and then air-dried for 1.5 hour at room temperature. The dried cloth was heat-treated for 20 minutes at 140° C. in a batch type hot air oven ("IPHH-2000", an inert oven manufactured by Tabaiesbeck Co., Ltd.) and washed with water. It was further washed with 5% aqueous sodium bicarbonate solution and rinsed three times with water and subsequently washed with 10% aqueous citric acid solution, rinsed three times with water, and finally washed with a JAFET standard detergent solution for household washing machine, rinsed with water and air-dried.

EXAMPLE 33

<Antibacterial Test>

An antibacterial test for the prepared nitrogenous carboxylic acid cellulose partial ester was carried out according to a standardized test method ("JIS L 1902: 1998 "Antibacterial activity test method for fibrous products" 8, a quantitative test) provided by Japanese Association for the Function Evaluation of Textile (JAFET).

Untreated cloth for control was prepared by a process wherein a cotton cloth was treated with 25% aqueous sodium hydroxide solution for an hour at room temperature, washed with water and dried, and thereafter washed with water and subsequently washed with 5% aqueous sodium bicarbonate solution, rinsed three times with water, washed with 10% aqueous citric acid solution, rinsed three times with water, and finally washed with household detergent solution for washing, rinsed with water and air-dried.

<Test Method>

Three pieces were prepared from each cloth by cutting it into square of about 18 mm in a side as test sample and subjected to high pressure vapor sterilization.

Each of these test pieces was seeded with the prescribed amount (about $2 \times 10^4$) of bacteria suspended in Nutrient Broth culture medium and the cultivation was conducted for 18 hours 37° C., and thereafter the respective viable counts were measured. An average value of the viable counts measured on 3 pieces of each specimen was estimated. The bacteriostatic activity and bactericidal activity were calculated according to the following equations:

The bacteriostatic activity=log (number of bacteria on standard cloth after cultivation)—log (number of bacteria on test cloth after cultivation)

The bactericidal activity=log (number of bacteria on standard cloth immediately after seed)—log (number of bacteria on test cloth after cultivation)

<Test Result>

Test results of antibacterial activity measured for the untreated cloth and the specimens prepared in Examples 1~3 are shown in table 1.

TABLE 1

|  | Bacteriostatic Activity | | | | Bactericidal Activity | | | |
| --- | --- | --- | --- | --- | --- | --- | --- | --- |
|  | Control Untreated Cloth | Example 1 Lysine | Example 2 Arginine | Example 3 Hystidine | Control Untreated Cloth | Example 1 Lysine | Example 2 Arginine | Example 3 Hystidine |
| *Staphylococcus Aures* (ATCC6538P) | 0.1 | 3.9 | 5.5 | 4.1 | −2.9 | 1.0 | 2.6 | 1.2 |
| *Klebsiella Pneumoniae* (ATCC4352) | 0.1 | 4.8 | 4.2 | 4.5 | −3.0 | 1.7 | 1.1 | 1.4 |
| MRSA (IID1677) | 0.2 | 5.5≦ | 5.5≦ | 5.5≦ | −2.5 | 2.9≦ | 2.9≦ | 2.9≦ |
| *Escherichia coli* (IFO3301) | 0.1 | 6.2≦ | 6.2≦ | 6.2≦ | −3.0 | 3.1≦ | 3.1≦ | 3.1≦ |
| *Pseudomonas Auruginosa* (IFO3080) | 0.3 | 6.2≦ | 6.2≦ | 6.2≦ | −2.9 | 3.1≦ | 3.1≦ | 3.1≦ |

Test results of antibacterial activity measured for the specimens prepared in Examples 20~32 are shown in table 2.

TABLE 2

|  |  | Bacteriostatic Activity | | Bactericidal Activity | |
| --- | --- | --- | --- | --- | --- |
| Example | Nitrogenous Carboxylic Acid | *Staphylococcus aures* (ATCC6538P) | *Klebsiella pneumoniae* (ATCC4352) | *Staphylococcus aures* (ATCC6538P) | *Klebsiella pneumoniae* (ATCC4352) |
| 20 | L-Lysine | 5.9≦ | 4.6 | 3.1≦ | 1.3 |
| 21 | L-Arginine | 4.5 | 3.9 | 1.7 | 0.6 |
| 22 | L-Lysine | 5.9≦ | 6.4≦ | 3.1≦ | 3.1≦ |
| 23 | L-Arginine | 4.9 | 6.4≦ | 2.1 | 3.1≦ |
| 24 | $N^\delta$-Nitro-L-Arginine | 4.9 | 6.1≦ | 2.2 | 2.9≦ |
| 25 | L-Phenylalanine | 5.9≦ | 6.2≦ | 2.9≦ | 2.9≦ |
| 26 | Glycine | 5.3 | 0.9 | 2.6 | −2.3 |
| 27 | β-alanine | 5.8≦ | 3.3 | 3.1≦ | 0.1 |
| 28 | γ-Aminobutyric acid | 5.8≦ | 0.1 | 3.1≦ | −3.1 |
| 29 | ε-Aminocaproic acid | 4.6 | 0.1 | 1.9 | −3.1 |
| 30 | 3-Aminocyclohexane carboxilic acid | 3.9 | 0.1 | 1.1 | −3.1 |
| 31 | Isonipechotinic acid | 4.7 | 0.0 | 1.9 | −3.2 |
| 32 | 4-Pyridioiobutyric acid | 3.0 | 0.5 | 0.2 | −2.8 |

It was confirmed from the above results that nitrogenous carboxylic acid cellulose partial esters have antibacterial property.

EXAMPLE 34

<Washing-resistance Test>

Using the cotton cloth prepared in Example 17, washing-resistance test of its antibacterial activity was conducted. The test was conducted in a high temperature accelerative washing method using a Washer washing machine according to the standardized test method provided by JAFET and the antibacterial activity before washing and after washing 5, 10 and 50 times was estimated. *Staphylococcus aures* (ATCC6538P) was employed as the test bacteria. The result is shown in table 3.

TABLE 3

|  | Bacteriostatic Activity | Bactericidal Activity |
| --- | --- | --- |
| Before washing | 5.9≦ | 3.1≦ |
| After washing 5 times | 5.0 | 2.3 |
| After washing 10 times | 4.4 | 1.7 |
| After washing 50 times | 4.3 | 1.6 |

It was confirmed from the above result that lysine cellulose partial ester has antibacterial and washing-resistant properties.

EXAMPLE 35

\<Combustion Test\>

Specimens, each having 10 mm in width and 100 mm in length were prepared from clothes A~D described below to conduct the combustion test.

A: a cotton cloth which was washed with water, and further washed with 5% aqueous sodium bicarbonate solution, rinsed three times with water, washed with 10% aqueous citric acid solution, rinsed three times with water, and finally washed with household detergent solution for washing, rinsed with water and air-dried (washed cloth)

B: a cotton cloth which was treated with 25% aqueous sodium hydroxide solution for a hour at room temperature, washed with water and dried, and further washed in the same manner as in the above A (untreated specimen)

C: the cotton cloth prepared in Example 2 (arginine/citrate specimen)

D: the cotton cloth prepared in Example 16 (arginine/phosphate specimen)

A terminal of each specimen fixed horizontally was ignited with a burner and the moving velocity of the combustion part was measured.

TABLE 4

| Specimen | Combustion Velocity |
| --- | --- |
| A. Washed cloth | 115 mm/min. |
| B. Untreated specimen | 119 mm/min. |
| C. Arginine/citrate specimen | 89 mm/min. |
| D. Arginine/phosphate specimen | Extinguished after 20 mm of combustion. |

It was confirmed from the above result that arginine cellulose partial ester has flame retardancy and washing-resistant property.

Comparative Example 1

A cotton cloth (200 mm×200 mm, 7.5 g) was treated with 25% aqueous sodium hydroxide solution for a hour at room temperature, washed with water and dried. This treated cotton cloth was allowed to uniformly absorb the total amount of the treating agent solution described in Example 1 and then air-dried for 3 hours at room temperature. The dried cloth was washed and air-dried in the same procedure as in Example 1 without being subjected to the heat-treatment. A part of the cloth was cut and a solution of ninhydrin in butanol was sprayed on it. Thereafter, it was heated for 10 minutes in an oven of 110° C. but no coloring was recognized, Comparative Example 2

The similar experiment as in Comparative Example 1 was conducted using the treating agent solution described in Example 2. As the result, no coloring was recognized, Comparative Example 3

The similar experiment as in Comparative Example 1 was conducted using the treating agent solution described in Example 3. As the result, no coloring was recognized.

INDUSTRIAL APPLICABILITY

According to the present invention, it became possible to provide a novel partial ester of a nitrogenous carboxylic acid with cellulose which is useful as an antibactreial agent and a flame retardant. Fibers made of partial ester of a nitrogenous carboxylic acid with cellulose have washing-resistant antibacterial properties and flame retardancy. Also, it became possible to provide an industrially advantageous process for preparing the partial ester of a nitrogenous carboxylic acid with cellulose which comprises subjecting directly cellulose with a nitrogenous carboxylic acid ester to heat processing.

The invention claimed is:

1. A partial ester of a nitrogenous carboxylic acid with cellulose or its salt, wherein said partial ester contains at least one of glucose unit represented by formula (I)

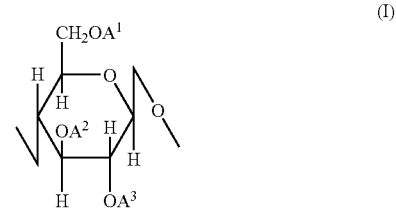

(I)

wherein
$A^1$, $A^2$, and $A^3$ independently represent a hydrogen atom or a nitrogenous acyl group represented by formula (II) provided that all of $A^1$, $A^2$, and $A^3$ are not hydrogen atoms

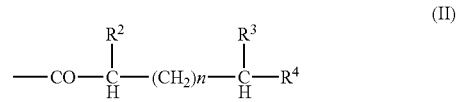

(II)

wherein
$R^2$ represents a hydrogen atom, an alkyl group having 1~6 carbon atoms, an amino group or a protonated amino group,
$R^3$ represents a hydrogen atom, an alkyl group having 1~6 carbon atoms or an aryl group,
$R^4$ represents a hydrogen atom, an alkyl group having 1~4 carbon atoms, a hydroxyl group, a mercapto group or a nitrogenous substituent represented by formulae (III) or (IV)

(III)

(IV)

wherein $R^5$, $R^6$ and $R^7$ independently represent a hydrogen atom, an alkyl group having 1~6 carbon atoms, an amino group, an amidino group, a nitroamidino group, a protonated amino group or a protonated amidino group, $R^5$ may bond with $R^2$, $R^3$ or $R^6$ to form a ring, and n represents an integer of 0~20, and wherein $R^2$ may bond with $R^3$ to form a ring;

with the proviso that when $R^2$ not an amino group or a protonated amino group, $R^4$ is any one of the nitrogenous substituents represented by the formulae (III) or (IV); and when $R^4$ is not any one of the nitrogenous substituents represented by the formulae (III) or (IV), $R^2$ is an amino group or a protonated amino group; and with a proviso that the nitrogenous carboxylic acid is not glycine, alanine, aminoenanthic acid, aminocaproic acid or p-aminobenzoic acid.

2. The partial ester of a nitrogenous carboxylic acid with cellulose or its salt as claimed in claim 1 wherein $R^2$ is an amino group, $R^3$ is a hydrogen atom or a phenyl group, $R^4$ is a hydrogen atom, a hydroxyl group or the nitrogenous substituent represented by formula (III),

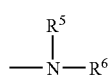
(III)

$R^5$ and $R^6$ are independently a hydrogen atom, an alkyl group having 1~6 carbon atoms, an amino group or an amidino group and n is an integer of 0~3.

3. The partial ester of a nitrogenous carboxylic acid with cellulose or its salt as claimed in claim 1 wherein said nitrogenous carboxylic acid is selected from the group consisting of lysine, arginine, ornithine, histidine and phenylalanine.

4. A fiber comprising a partial ester of a nitrogenous carboxylic acid with cellulose or its salt according to claim 1.

5. The fiber as claimed in claim 4, wherein $R^2$ is an amino group, $R^3$ is a hydrogen atom or phenyl group, $R^4$ is a hydrogen atom, a hydroxyl group or a nitrogenous substituent represented by formula (III),

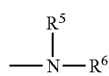
(III)

wherein $R^5$ and $R^6$ are independently a hydrogen atom, an alkyl group having 1~6 carbon atoms, an amino group or an amidino group and n is an integer of 0~3.

6. The fiber as claimed in claim 4, wherein said nitrogenous carboxylic acid is at least one member selected from the group consisting of lysine, arginine, ornithine, histidine and phenylalanine.

7. A process for preparing a partial ester of a nitrogenous carboxylic acid with cellulose or its salt according to claim 1, comprising mixing cellulose with a nitrogenous carboxylic acid ester represented by formula (X) to obtain a mixture, and heat-treating the mixture, wherein

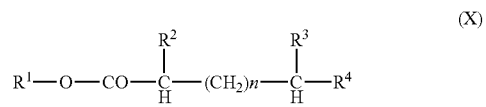
(X)

$R^1$ represents an alkyl group having 1~7 carbon atoms, an aryl group or an aralkyl group, $R^2$ represents a hydrogen atom, an alkyl group having 1~6 carbon atoms, an amino group or a protonated amino group, $R^3$ represents a hydrogen atom, an alkyl group having 1~6 carbon atoms or an aryl group, $R^4$ represents a hydrogen atom, an alkyl group having 1~4 carbon atoms, a hydroxyl group, a mercapto group or a nitrogenous substituent represented by formulae (III) or (IV)

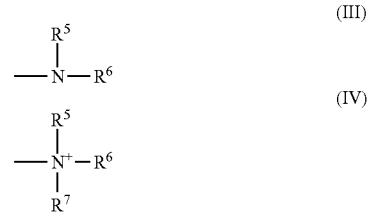
(III)

(IV)

wherein $R^5$, $R^6$ and $R^7$ independently represent a hydrogen atom, an alkyl group having 1~6 carbon atoms, an amino group, an amidino group, a nitroamidino group, a protonated amino group or a protonated amidino group, $R^5$ may bond with $R^2$, $R^3$ or $R^6$ to form a ring, and n represents an integer of 0~20, and wherein $R^2$ may bond with $R^3$ to form a ring;

with the proviso that when $R^2$ not an amino group or a protonated amino group, $R^4$ is any one of the nitrogenous substituents represented by the formulae (III) or (IV); and when $R^4$ is not any one of the nitrogenous substituents represented by the formulae (III) or (IV), $R^2$ is an amino group or a protonated amino group.

8. A process for preparing fibrous partial ester of a nitrogenous carboxylic acid with cellulose or its salt according to claim 4, comprising mixing cellulose fibers with a nitrogenous carboxylic acid ester represented by formula (X) to obtain a mixture, and heat-treating the mixture, wherein

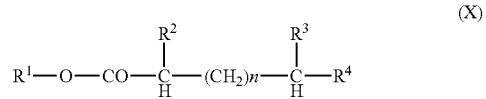
(X)

$R^1$ represents an alkyl group having 1~7 carbon atoms, an aryl group or an aralkyl group, $R^2$ represents a hydrogen atom, an alkyl group having 1~6 carbon atoms, an amino group or a protonated amino group, $R^3$ represents a hydrogen atom, an alkyl group having 1~6 carbon atoms or an aryl group, $R^4$ represents a hydrogen atom, an alkyl group having 1~4 carbon atoms, a hydroxyl group, a mercapto group or a nitrogenous substituent represented by formulae (III) or (IV)

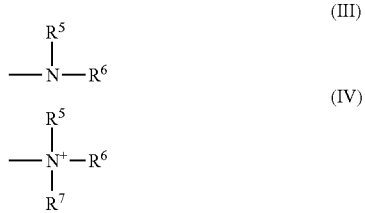

wherein $R^5$, $R^6$ $R^7$ independently represent a hydrogen atom, an alkyl group having 1~6 carbon atoms, an amino group, an amidino group, a nitroamidino group, a protonated amino group or a protonated amidino group, $R^5$ may bond with $R^2$, $R^3$ or $R^6$ to form a ring, and n represents an integer of 0~20, and wherein $R^2$ may bond with $R^3$ to form a ring;

with the proviso that when $R^2$ is not an amino group or a protonated amino group, $R^4$ is any one of the nitrogenous substituents represented by the formulae (III) or (IV); and when $R^4$ is not any one of the nitrogenous sub stituents represented by the formulae (III) or (IV), $R^2$ is an amino group or a protonated amino group.

9. The process as claimed in claim 7, wherein said heat-treating is at a temperature ranging from 100 to 200° C. for 1 to 100 minutes.

10. The process as claimed in claim 8, wherein said heat-treating is at a temperature ranging from 100 to 200° C. for 1 to 100 minutes.

* * * * *